(12) United States Patent
Sarén (10) Patent No.: US 8,798,943 B2
(45) Date of Patent: Aug. 5, 2014

(54) DRAINABILITY MEASUREMENT

(75) Inventor: Matti-Paavo Sarén, Kajaani (FI)

(73) Assignee: Metso Automation Oy, Helsinki (FI)

( * ) Notice: Subject to any disclaimer, the term of this patent is extended or adjusted under 35 U.S.C. 154(b) by 736 days.

(21) Appl. No.: 13/001,469

(22) PCT Filed: Jun. 26, 2009

(86) PCT No.: PCT/FI2009/050577
§ 371 (c)(1),
(2), (4) Date: Feb. 7, 2011

(87) PCT Pub. No.: WO2010/000931
PCT Pub. Date: Jan. 7, 2010

(65) Prior Publication Data
US 2011/0153230 A1    Jun. 23, 2011

(30) Foreign Application Priority Data

Jun. 30, 2008  (FI) ...................... 20085675

(51) Int. Cl.
*G01N 15/04* (2006.01)
*B01D 21/00* (2006.01)
*G06F 17/40* (2006.01)
*G06F 19/00* (2011.01)
*B01D 21/02* (2006.01)

(52) U.S. Cl.
CPC ............... *G01N 15/04* (2013.01); *B01D 21/10* (2013.01); *G06F 17/40* (2013.01); *G06F 19/00* (2013.01)
USPC ............ 702/50; 73/1.16; 73/53.04; 73/61.62; 73/61.63; 702/100; 702/187; 702/189

(58) Field of Classification Search
CPC ...... B01D 11/00; B01D 11/102; B01D 17/00; B01D 21/00; B01D 21/10; B01D 23/00; B01D 23/20; B01D 23/28; B01D 29/00; B01D 29/085; B01D 29/88; B01D 29/92; B67C 11/00; G01D 7/00; G01D 21/00; G01F 5/00; G01N 15/00; G01N 15/02; G01N 15/04; G01N 33/00; G01N 33/34; G01N 33/343; G06F 11/00; G06F 11/30; G06F 11/32; G06F 17/00; G06F 17/40; G06F 19/00
USPC ............. 73/1.01, 1.16, 1.34, 1.36, 1.73, 1.74, 73/53.01, 53.03, 53.04, 61.41, 61.62, 73/61.63, 61.64, 61.65, 61.68, 61.71, 73/61.72, 61.73, 432.1, 865.8, 865.9, 866; 209/1, 132, 155; 210/600, 767; 377/1, 377/19, 21; 702/1, 33, 45, 48, 50, 85, 100, 702/105, 127, 182, 187, 189; 703/6, 9; 708/100, 105, 200
IPC .......... B01D 11/00, 11/02, 17/00, 21/00, 21/10, B01D 23/00, 32/20, 23/28, 29/00, 29/085, B01D 28/88, 29/92; B67C 11/00; G01D 7/00, G01D 21/00; G01F 5/00; G01N 15/00, 15/04, G01N 33/00, 33/34, 33/343; G06F 11/00, G06F 11/30, 11/32, 17/00, 17/40, 19/00
See application file for complete search history.

(56) References Cited

U.S. PATENT DOCUMENTS

| | | | | |
|---|---|---|---|---|
| 2,572,436 A | * | 10/1951 | Boucher et al. | 73/61.63 |
| 2,599,742 A | * | 6/1952 | Boucher et al. | 73/61.63 |
| 2,602,325 A | * | 7/1952 | Campbell et al. | 73/53.03 |
| 2,615,329 A | * | 10/1952 | Witham George S | 73/53.04 |
| 2,734,378 A | * | 2/1956 | Meyers | 73/61.63 |
| 3,144,763 A | * | 8/1964 | Mayo | 73/53.04 |
| 3,186,215 A | * | 6/1965 | Danforth | 73/53.04 |
| 3,198,006 A | * | 8/1965 | Williams | 73/53.04 |
| 3,206,969 A | * | 9/1965 | Irving | 73/53.04 |
| 3,330,151 A | * | 7/1967 | Reinhall | 73/53.04 |
| 3,452,587 A | * | 7/1969 | Danforth et al. | 73/53.04 |
| 3,628,667 A | * | 12/1971 | Somora et al. | 210/519 |
| 3,682,444 A | * | 8/1972 | Reinhall | 241/33 |
| 4,406,159 A | * | 9/1983 | Yanishevsky | 73/53.04 |
| 5,365,775 A | | 11/1994 | Penniman | |
| 5,491,340 A | | 2/1996 | Saarinen | |
| 5,954,922 A | | 9/1999 | Ramarao | |
| 6,523,395 B1 | * | 2/2003 | Kahkonen | 73/53.04 |
| 2006/0096961 A1 | | 5/2006 | Kahkonen et al. | |
| 2006/0196621 A1 | | 9/2006 | Johansson | |

FOREIGN PATENT DOCUMENTS

| FI | 104855 B | 4/2000 |
|---|---|---|
| FI | 113383 B | 4/2004 |
| JP | U-61-174628 | 10/1986 |
| JP | U-63-193322 | 12/1988 |
| WO | WO 00/02032 A1 | 1/2000 |

OTHER PUBLICATIONS

Swodzinski et al., "Mathematic Models of Canadian Standard Freeness (CSF) and Schopper-Riegler Freeness (SR)," *IPC Technical Paper Series*, May 1986, pp. 1-16, No. 172, Appleton, Wisconsin, USA.

"Drainability of Pulp by the Schopper-Riegler Method," *Scandinavian Pulp, Paper and Board Testing Committee*, SCAN-C19:65, accepted Oct. 1964, pp. 1-4.

"Freeness of pulp (Canadian standard method)," 1999, pp. 1-9, the Pulp Properties Committee of the Process and Product Quality Division, TAPPI.

Finnish Search Report for corresponding Finnish Patent Application No. 20085675, dated Mar. 3, 2009 (w/ English translation).

International Search Report for International Patent Application No. PCT/FI2009/050577, mailed on Oct. 21, 2009.

International Preliminary Report on Patentability for International Patent Application No. PCT/FI2009/050577, dated Nov. 17, 2010.

Jun. 11, 2013 Japanese Office Action issued in JP 2011-515505 (with English-language Translation).

\* cited by examiner

*Primary Examiner* — Edward Cosimano
(74) *Attorney, Agent, or Firm* — Oliff PLC (57) ABSTRACT

A measurement device measures a liquid flow discharged from a funnel in a lower branch and/or a side branch. A modelling function is established between liquid flows received with the funnel and/or liquid flows discharged through the lower branch and/or the side branch. In drainability measurement, a sensor measures the flow through a wire out of a measurement chamber at least at two points in time. A processor establishes a parameter descriptive of the drainability from flows measured at the different points in time based on a modelling function stored in a memory.

17 Claims, 10 Drawing Sheets

DRAINABILITY MEASUREMENT

FIELD

The invention relates to the modelling of a drainability measurement, and to a drainability measurement, and to measuring devices associated therewith.

BACKGROUND

Accurate measurement and adjustment of the properties of paper pulp are required in the manufacture of good-quality paper. In the drainability measurement (such as freeness or Schopper-Riegler value) of paper pulp, the speed at which the paper pulp can be separated from water is determined empirically. Drainability depends on a plurality of factors, such as fibres, pulp processing (e.g. mechanical/chemical), amount of fine substance, temperature, consistency and measuring device.

One of the most known drainability measurement methods is CSF (Canadian Standard Freeness). This measurement method is a standard and it is presented in more detail in publication T 227 om-99, Freeness of pulp, TAPPI, 1999. At the beginning of the CSF drainability measurement, exactly one liter of sample is taken into a measurement chamber. The lower lid is opened, and the sample is allowed to settle in the reservoir, whereby some pulp is descended onto a wire at the lower part of the reservoir. When 5 seconds have lapsed from the opening of the lower lid, the air valve is opened, whereby water starts to be discharged from the pulp sample through the wire and the pulp accumulating on the wire into a funnel. Part of the water flows out of a lower branch of the funnel, which is thought to release water as a predetermined flow. Water accumulating over a predetermined constant volume, in turn, flows out of a side branch if the flow of liquid flowing into the funnel exceeds a predetermined flow. In drainability measurement, it is exactly the amount of water flown from the side branch that is measured with a measuring glass, and this amount of water corresponds to the drainability, the CSF value. The measurement is usually performed manually. The measurement is cumbersome and sensitive to changes in both consistency and temperature. In addition, at low CSF values, the measurement is inaccurate.

Another known drainability determination method is the so-called Schopper-Riegler method, which is presented in publication SCAN-C 19:65, Scandinavian pulp, paper and board, Testing committee, approved in 1964. This measurement, too, is based on the flow of water flowing through the wire through the lower branch and the side branch, and the water flown through the side branch determines the drainability. This measurement, too, is usually performed manually. As the previous measurement, this measurement, too, is cumbersome and sensitive to changes in both consistency and temperature. In addition, at extreme values, in particular, the SR measurement is inaccurate.

In addition, Finnish patent 104855 discloses a solution, wherein the drainability can be determined computationally by measuring the flow from the measurement chamber, by determining the point in time when the flow from the measurement chamber corresponds to a predetermined flow, and by establishing the drainability as a function of the amount flown from the measurement chamber up to a determined point in time. However, since this solution, too, is associated with inaccuracy, there exists a need for a more accurate drainability measurement than the previous ones.

BRIEF DESCRIPTION

The object of the invention is to provide an improved method and a device for implementing the method. This is achieved by a method of modelling the drainability measurement of a suspension. Further, the method comprises receiving known flows with a funnel, each of which fills the funnel in such a manner that liquid flows from a side branch; measuring the flows of the lower branch and/or the side branch with the different flows received with the funnel; and establishing a modelling function based on the measurements between the flows of the lower branch and/or the side branch and the flows received with the funnel.

The invention also relates to a method of measuring a suspension, the method comprising receiving a sample of a predetermined volume in a measurement chamber; and allowing the suspension to flow out of the measuring chamber through a wire. The method further comprises measuring the flow out of the measurement chamber at least at two points in time; establishing a parameter descriptive of the drainability of the suspension by a predetermined modelling function from the flows measured at the different points in time.

The invention further relates to a measurement device for modelling the drainability measurement of a suspension. The measurement device comprises a funnel, a meter and a memory, the funnel comprising a side branch and a lower branch being configured to receive known liquid flows, each of which is larger than the flow of the lower branch of the funnel; the meter is configured to measure the liquid flow discharged from the funnel with the liquid flows received by the funnel in at least one of the following: lower branch, side branch; and the memory is configured to store the modelling function when the modelling function is based on a dependency between the liquid flows received with the funnel and the liquid flows discharged from the funnel in at least one of the following: lower branch, side branch.

The invention also relates to a measurement device for measuring a suspension, the measurement device comprising a measurement chamber of a predetermined volume and a wire, the measurement chamber is configured to receive a suspension sample and allow the suspension sample to flow out of the measurement chamber through the wire. The measurement device comprises a sensor for measuring the flow out of the measurement chamber at least at two different points in time; a memory, in which a predetermined modelling function is stored; and a processor configured to establish a parameter descriptive of the drainability of the suspension based on the predetermined function stored in the memory from the flows measured at the different points in time.

Preferred embodiments of the invention are described in the dependent claims.

The method and arrangement of the invention provide a plurality of advantages. The drainability measurement is rendered more accurate and the measurement result may be set to correspond to the result of the desired measurement device.

LIST OF FIGURES

In the following, the invention will be described in more detail in connection with preferred embodiments with reference to the accompanying drawings, in which.

DESCRIPTION OF EMBODIMENTS

Figure 1:
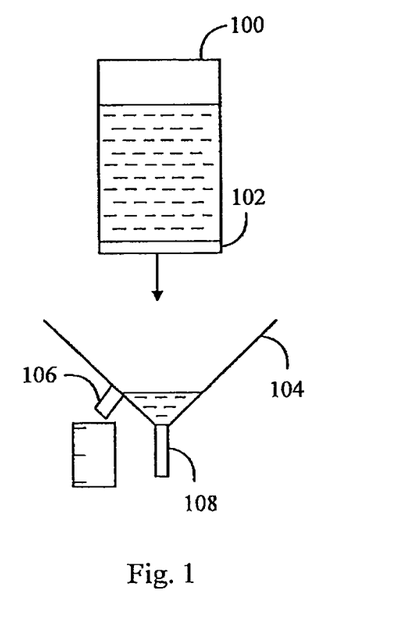
FIG. 1 shows a standard drainability measurement.

Let us first study a prior art drainability measurement based on a standard. A suspension sample is first taken to a measurement chamber 100, whose volume is known, 1 dm$^3$, for example. The suspension may contain for instance water and particles of a solid substance, such as fillers, fine materials and/or fibres, which, in turn, may be plant fibres, wood fibres and/or synthetic fibres, for example. The suspension may be pulp for making paper or board, for example. Referring to FIG. 1, a full measurement chamber of suspension is then allowed to flow through a wire 102 towards a funnel 104 comprising a lower branch 108 and a side branch 106. Part of the suspension entering the funnel 104, the suspension having been filtered mainly into water when passing the wire 102 and the cake produced onto the wire, flows out of the funnel 104 through the lower branch 108. In known measurements, this flow is assumed to be a constant flow, whose value is considered about 8.83 ml/s in a CSF measurement and about 6.71 ml/s in a Schopper-Riegler measurement, for example. Part of the suspension also flows through the side branch 106 out of the funnel 104 and the amount of suspension discharged through the side branch is measured. The amount of suspension measured and discharged from the side branch 106 determines the drainability of the suspension.

In prior art solutions, the flow through the lower branch 108 is not completely constant, but varies. Since the flow of the side branch 106 depends on the flow of the lower branch 108, the flow variations in the lower branch 108 affect the drainability measurement result.

In the solution presented, the drainability measurement can be modelled. In modelling, liquid and/or suspension may be supplied to a funnel 104 of the desired kind at several different flows. Each flow supplied to the funnel 104 may be used to measure the flow of the side branch 106, the flow of the lower branch 108 and the flow of both the side branch 106 and the lower branch 108.

Figure 2:
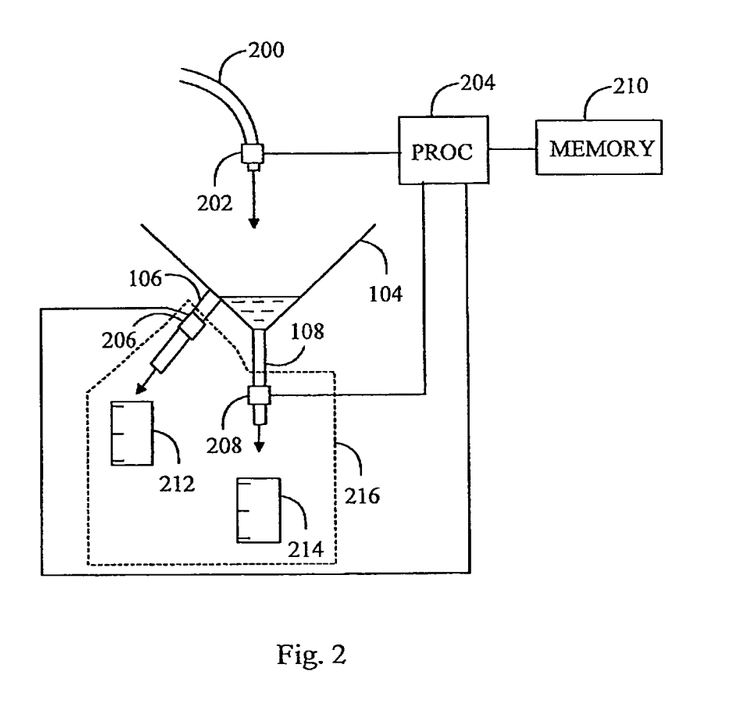
FIG. 2 shows a measurement device for modelling a drainability measurement.

FIG. 2 shows a measurement device for modelling the drainability measurement of a suspension. The measurement device may comprise a liquid source 200, a flow sensor 202 and a processor 204. The liquid source 200 may direct known liquid flows filling the funnel 104 such that liquid flows from the side branch 106 to each desired funnel 104 used in the drainability measurement of the suspension and comprising a lower branch 108 and a side branch 106. In this case, each of the liquid flows is thus larger than the flow of the lower branch 108 of the funnel 104. The liquid used in the modelling may be water or a suspension of the desired kind. The flow sensor 202 may measure the liquid flow directed to the funnel 104. The flow sensor 206 may measure the flow of the side branch 106 with the liquid flows supplied to the funnel 104. Alternatively or in addition, the flow sensor 208 may measure the flow of the lower branch 108 with the liquid flows supplied to the funnel 104. The processor 204 may establish a modelling function descriptive of the dependency of the flows of the lower branch 108 of the funnel 104 on the liquid flows supplied to the funnel 104. Alternatively or in addition, the processor 204 may establish a modelling function descriptive of the dependency of the flows of the side branch 106 of the funnel 104 on the liquid flows supplied to the funnel 104. Once a suitable modelling function is established, it may be stored in the memory 210 and the drainability of the actual suspension to be measured may then be measured without the funnel 104.

Instead of or in addition to the flow sensor 202, one or more valves or another corresponding structure, for example, may also be used and arranged to allow predetermined flows into the funnel 104.

Instead of or in addition to the flow sensor 206, a collection vessel 212 may also be used as the meter 216, into which the liquid flowing from the side branch 106 is collected. The collection vessel 212 may be weighed all the time or at the desired points in time for determining the amount of liquid in the collection vessel 212. The flow incoming to the collection vessel 212 at different points in time may be established based on the amount of liquid and the time. Instead of or in addition to weighing, the volume of the liquid accumulated may be determined in the desired measurement manner continuously or at the desired points in time.

Instead of or in addition to the flow sensor 208, a collection vessel 214 may also be used as the meter 216, into which the liquid flowing from the lower branch 108 is collected. The collection vessel 214 may be weighed all the time or at the desired points in time for determining the amount of liquid in the collection vessel 214. The flow incoming to the collection vessel 214 at different points in time may be established based on the amount of liquid and the time. Instead of or in addition to weighing, the volume of the liquid accumulated may be determined in the desired measurement manner continuously or at the desired points in time.

The flow measurements, weighings and/or volume determinations may be performed automatically or manually.

Figure 3:
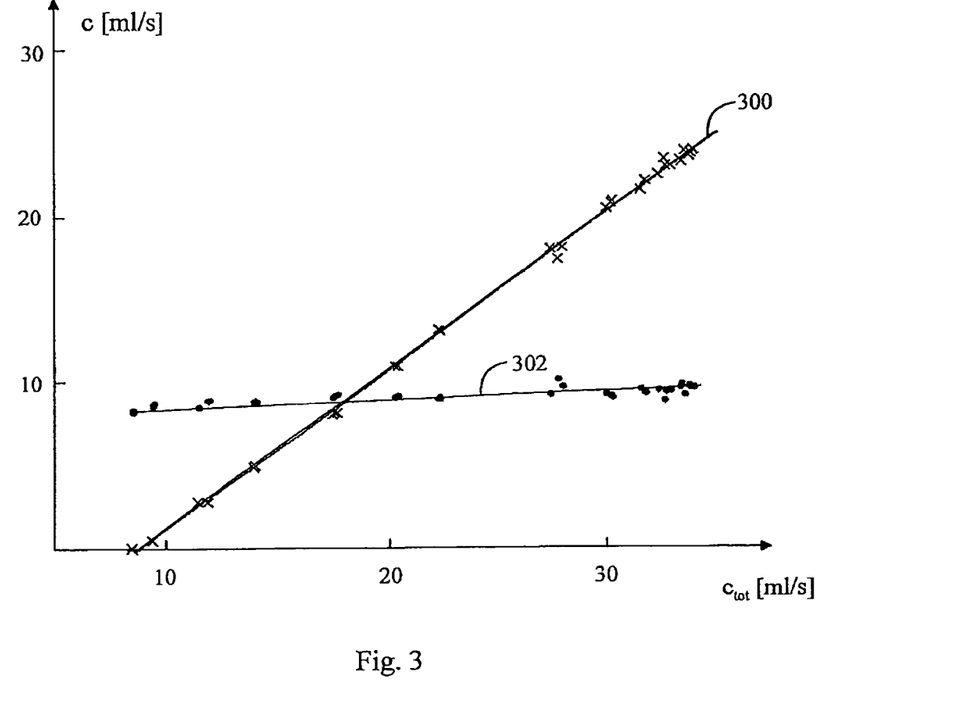
FIG. 3 shows flows of a side branch and a lower branch as a function of the total flow.

FIG. 3 shows a flow 300 measured from the side branch 106 of the funnel and a flow 302 from the lower branch 108. The vertical axis is flow in milliliters per second and the horizontal axis is the flow directed to the funnel 104 in milliliters per second. The crosses and points represent the measurement values and the lines are lines configured to the measurement values. In this example, as side branch 106 flow $c_{side}$ in a linear adaptation is obtained, as a function of flow $c_{tot}$ directed to the funnel and flowing out of the measurement chamber 100

$$c_{side}(c_{tot}) = (0.959 * c_{tot} - 8.3031) \text{ml/s}, \quad (1)$$

when the flow is more than 8.3031 ml/s. Otherwise, $c_{side}$ is 0. Accordingly, the absolute value $|c_{side}(2) - c_{side}(1)|$ of any two different flows of the side branch 106 of the funnel 104 is less than the absolute value $|c_{tot}(2) - c_{tot}(1)|$ of the difference between two flows measured. In this example, the absolute value of the difference between two different is $0.959*[c_{tot}(2) - c_{tot}(1)]$.

Correspondingly, as the flow of the lower branch 108 is obtained $$c_{lower}(c_{tot}) = (0.041 * c_{tot} + 8.3031) \text{ml/s} \quad (2)$$

when the flow is more than 8.3031 ml/s.

This example also shows that the flow of the lower branch 108 should have been a constant flow, but it was not. The constant part (8.3031 ml/s) of formula (2) differs from the constant value (8.83 ml/s) and the flow is dependent on the flow directed to the funnel 104 by coefficient 0.041. For example, function $f=0.959*c_{tot}-8.3031$ may be stored as a predetermined modelling function in the memory 210.

The functions defined may be general and apply to all pulp grades or each function may apply to some pulp grade type comprising a plurality of pulp grades. Each function may also be determined to apply to only one pulp grade. This being so, the constant value and/or the coefficient may be different for different pulps. Instead of linear functions, the values measured may also be inserted in non-linear functions, but it does not necessarily bring about much added accuracy.

Figure 4:
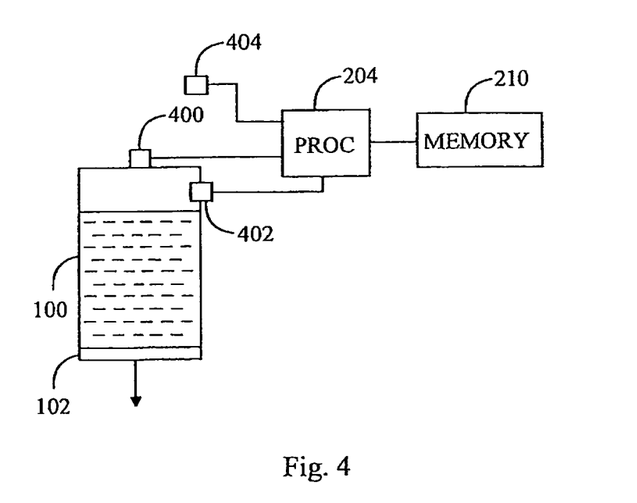
FIG. 4 shows a drainability measurement.

FIG. 4 shows a measurement device intended for the measurement of a suspension. The measurement device comprises a measurement chamber 100 of a predetermined volume for receiving a sample of the suspension. The measurement device may also comprise a wire 102 for filtering the suspension sample as it flows through the wire 102 out of the measurement chamber 100. The wire 102 may be a wire used in the CSF or Schopper-Riegler method, for example, and it may be manufactured in the manner described in Finnish patent 113383. Alternatively, the wire 102 may be any structure slowing down the flow of liquid and momentarily accumulating the solids in the suspension. The wire 102 may generate, on top thereof, a pulp cake from the solids of the suspension, the cake preventing the solids in the suspension from being discharged from the measurement chamber 102 by filtering. The measurement device further comprises a sensor 400 for measuring the flow out of the measurement chamber 100 at least at two different points in time. The sensor 400 may be any flow meter, known per se. The sensor 400 may be a liquid level height meter operating with ultrasound, for example. Since the measurement chamber 100 is known, the flow of the suspension discharged from the measurement chamber 100 can be determined from the change in the level of the suspension. The flow may be measured in volume units (liters or cubic meters, for example) in a time unit (a second, for example).

The measurement device further comprises a processor 204 and a memory 210. The processor 204 establishes a parameter descriptive of the drainability of the suspension based on the flows measured at the different points in time by means of a predetermined function stored in the memory 210.

For example, the CSF value according to the standard may be produced as an integral $$CSF = \int_{t_1}^{t_2} c_{side} \, dt = \int_{t_1}^{t_2} f_{known}(c_{tot}) \, dt, \qquad (3)$$

wherein $f_{known}$ is a function predetermined by measurements, $t_1$ is the moment when the suspension starts to be discharged from the measurement chamber 100, or $t_1$ is the moment when the suspension starts to flow from the side branch 106, and $t_2$ is some moment sufficiently remote, when the flow of the side branch 106 has stopped. The integral may also be converted into the form $$CSF = \int_{c_1}^{c_2} c_{side} \, dc = \int_{c_1}^{c_2} f_{known}(c_{tot}) \, dc, \qquad (4)$$

wherein $c_1$ is the smallest flow with which there is flow in the side branch 106, and $c_2$ is the largest flow measured. Flow $c_1$ may be measured and, in the linear model shown by way of example, it is 8.3031 ml/s.

The CSF value may be determined based on equation (4) also discretely by summing suspension amounts cΔt produced at different points in time $$CSF = \sum_{i=1}^{N} c_i^{side} \Delta t_i = \sum_{i=1}^{N} f_{known}(c_i^{tot}) \Delta t_i, \qquad (5)$$

wherein i is summing index, $c_i^{side}$ is the $i^{th}$ determined flow of the side branch 106, $c_i^{tot}$ the is $i^{th}$ flow out of the measurement chamber 100 and $\Delta t_i$ is the duration in time of the $i^{th}$ flow.

Instead of standard measurements, other drainability values and parameters associated therewith may also be determined by modifying a predetermined function in the desired manner.

In addition, the funnel 104 may be part of the laboratory measurement device of a paper mill. By adapting the functions in a suitable manner, the solution presented may be used in such a manner that the results obtained correspond to the laboratory measurements of said mill.

The measurement device may perform the measurement as a measurement corresponding to the standard. In this case, the processor 204 may produce a flow corresponding to each flow of the side branch 106 of the funnel 104 used in the measurement according to the standard from each flow measured that is larger than a predetermined flow with a predetermined function according to which the absolute value of the difference of any two different flows of the side branch 106 of the funnel 104 is less than the absolute value of the difference of two different flows measured. The predetermined flow may be the constant flow of the CSF method, about 8.83 ml/s or the about 6.71 ml/s of the Schopper-Riegler method, for example.

In order to perform a measurement corresponding to the standard, the processor 204 may also produce a flow corresponding to the flow of the lower branch 108 as a predetermined function of the flow measured, and delete the flow produced from each flow measured for producing a flow corresponding to the flow of the side branch 106.

The processor 204 may produce a parameter descriptive of the drainability based on flows corresponding to the flows of the side branch 106. In this case, the processor 204 may establish, for instance, the liquid volume produced by flows corresponding to the flows of the side branch 106, and the processor 204 may establish a parameter descriptive of the drainability based on the liquid volume produced.

The processor 204 may also measure the time taken up by the flow measured to change from a first flow into a second flow to establish a parameter descriptive of the drainability of the suspension.

The processor 204 may measure the time taken by a flow measured to change from a first predetermined flow into a second predetermined flow to establish a parameter descriptive of the drainability of the suspension. In this case, the first predetermined flow may be 12 ml/s, for example, and the second predetermined flow may be 9 ml/s, for example.

The measurement of the time taken up by a change between two different flows enables different information to be obtained about the drainability than by merely a measurement simulating a measurement according to the standard. When flow criteria are suitable set, the production speed of the pulp cake produced on the wire 102 may be estimated. This information, in turn, enables the determination of how much liquid is discharged from the measurement chamber 100 rapidly and/or how much liquid is discharged from the measurement chamber 100 slowly. The liquid flow out of the measurement chamber 100 may be rapid at first, but slow down clearly when the solids of the suspension are accumulated on top of the wire 102. This enables the determination of FWV (Free Water Value), for example, which depicts the amount of rapidly discharged water in a drainability process. The time taken up by a change between two different flows and/or the FWV may be used to specify the separation for even such suspensions that have the same drainability in a measurement simulating a measurement according to the standard.

The measurement device may further comprise at least one thermometer 402 and an ultrasound meter 400 for measuring the surface level for determining the flow from the measurement chamber 100. The thermometer 402 may measure the temperature of the suspension in the measurement chamber 100. A thermometer 404 may measure the temperature from gas that flows in place of the discharged suspension into the measurement chamber 100. Since indoor air is most usually involved, this temperature may be assumed to be 295 K, for example, even without measurement.

The processor 204 may determine the proportion k of gas and/or suspension in the measurement chamber 100 based on the flow measured and/or the surface level of the suspension. The gas is usually air. The proportion of gas may be determined for instance in such a manner that k=0 when a maximum amount of suspension is present in the measurement chamber 100 (immediately after sampling before measurement), and k=1 when a maximum amount of gas desired/used is present in the measurement chamber 100 (after measurement). The processor 204 may then determine gas temperature $T_k$ in the measurement chamber 100 based on the proportion of gas and/or suspension in the measurement chamber 100. With the above assumptions, the gas temperature $T_k$ in the measurement chamber 100 may be estimated from the extreme values of variable k:

$$T_k = (V_1 T_1 + k V_2 T_2)/(V_1 + k V_2), \quad (6)$$

wherein $T_1$ is gas temperature when a maximum amount of suspension is present in the measurement chamber, $T_2$ is gas temperature when a minimum amount of suspension is present in the measurement chamber, $V_1$ is gas volume when a maximum amount of suspension is present in the measurement chamber, $V_2$ is gas volume temperature when a minimum amount of suspension is present in the measurement chamber. $T_1$ may be the temperature of the suspension, 350 K, for example. $T_2$ may be estimated to be room temperature, 295 K, for example. $T_2$ may also be measured with the thermometer 404. A temperature-dependent correction coefficient b may be produced for the surface height of the liquid as follows:

$$b = \sqrt{(T_2/T_k)}. \quad (7)$$

In the above formulas, temperatures are given in Kelvin. The processor 104 may correct the height result of the liquid level based on a change in the velocity of sound in the gas as a function of the temperature measured. In this case, the corrected distance L between the sensor and the liquid level may be expressed as follows, for example:

$$L = L_{measured} * b, \quad (8)$$

wherein $L_{measured}$ is a temperature-uncorrected measurement result.

The volume of suspension $V_s$, in turn, may be produced from the measured level height L as follows $$V_s = f(L), \quad (9)$$

wherein function f depends on the geometry (dimensions and shape) of the measurement chamber 100. The volume of gas may then be expressed as:

$$V_{gas} = V_0 - V_s, \quad (10)$$

wherein $V_0$ is the volume of the measurement chamber, which may be found out by a measurement, for example.

Figure 5:
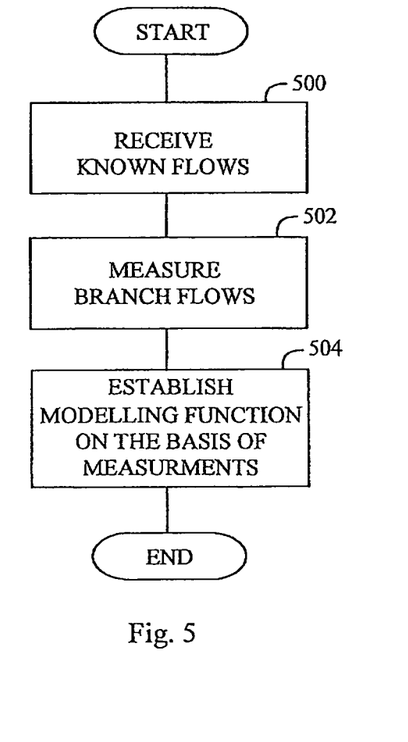
FIG. 5 shows a flow diagram of a method of establishing a model.

FIG. 5 shows the flow diagram of a method associated with modelling. In step 500, the funnel 104 is used to receive known flows, each of which fills the funnel 104 in such a manner that liquid flows from the side branch 106. In step 502, the flows of the lower branch 108 and/or the side branch 106 are measured at the different flows received with the funnel 104. In step 504, a modelling function based on the measurements is established between the flows of the lower branch 108 and/or the side branch 106 and the flows received with the funnel.

Figure 6:
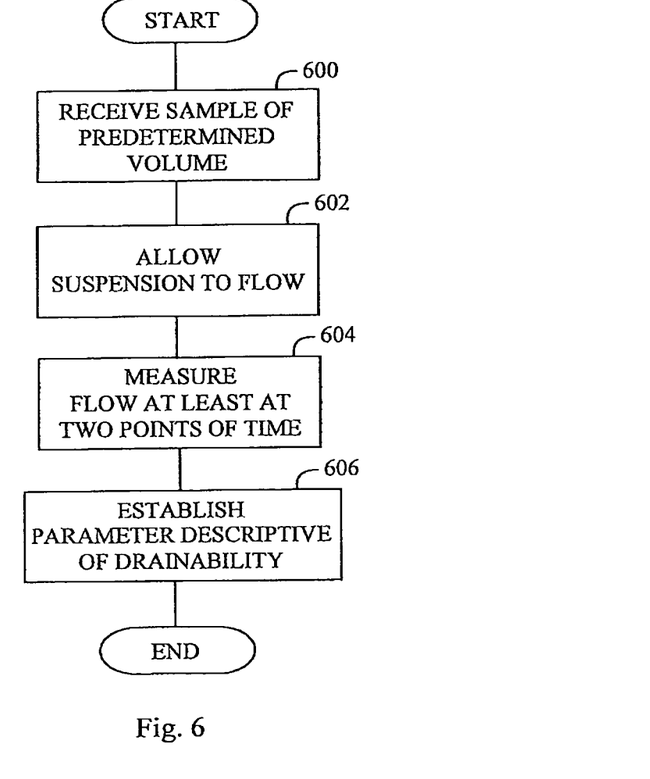
FIG. 6 shows a flow diagram of a drainability measurement.

FIG. 6 shows a flow diagram of a method associated with measurement. In step 600, a sample of a predetermined volume is received in the measurement chamber 100. In step 602, the suspension is allowed to flow out of the measurement chamber 100. In step 604, the flow from the measurement chamber 100 is measured at least at two points of time. In step 606, a parameter descriptive of the drainability of the suspension is established with a predetermined modelling function from the flows measured at the different points in time.

Figure 7:
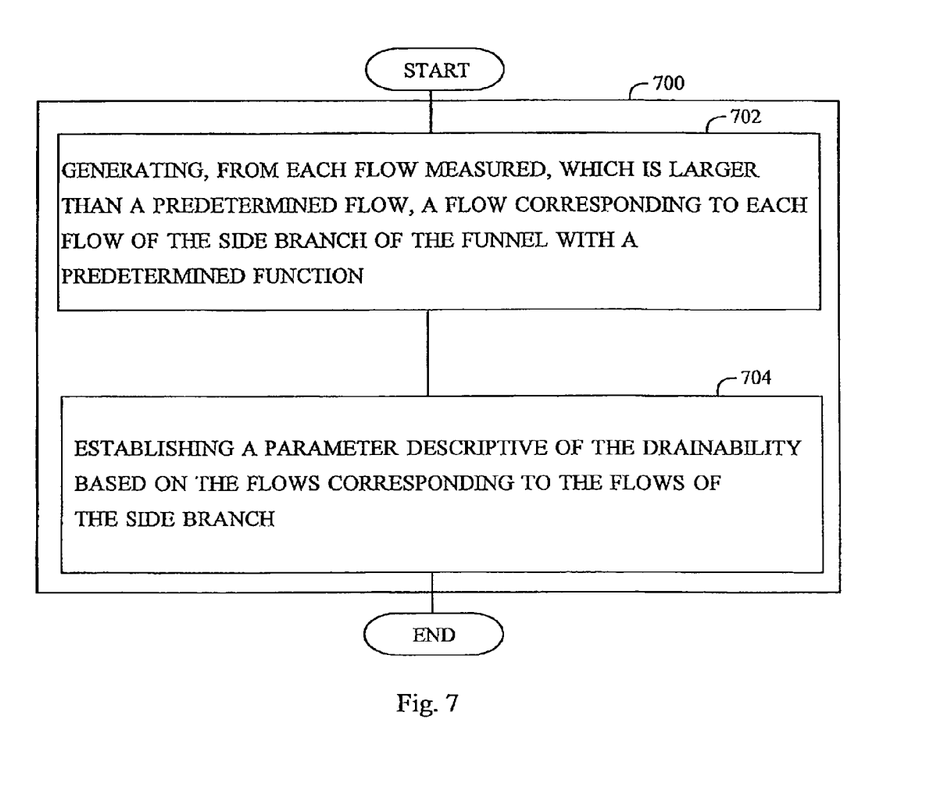
FIG. 7 shows a flow diagram of a method of generating a flow and establishing a corresponding parameter descriptive of drainability.

FIG. 7 shows a flow diagram 700 of a method of generating a flow and establishing a corresponding parameter descriptive of drainability, In step 702, the method involves performing the measurement as a measurement corresponding to a standard by generating, from each flow measured that is larger than a predetermined flow, a flow corresponding to each flow of the side branch of the funnel used in the measurement according to the standard with a predetermined function, according to which the absolute value of the difference between the two different flows of the side branch of the funnel is less than the absolute value of the difference between the two different flows measured. In step 704, the method proceeds to establishing a parameter descriptive of the drainability based on the flows corresponding to the flows of the side branch from step 702.

Figure 8:
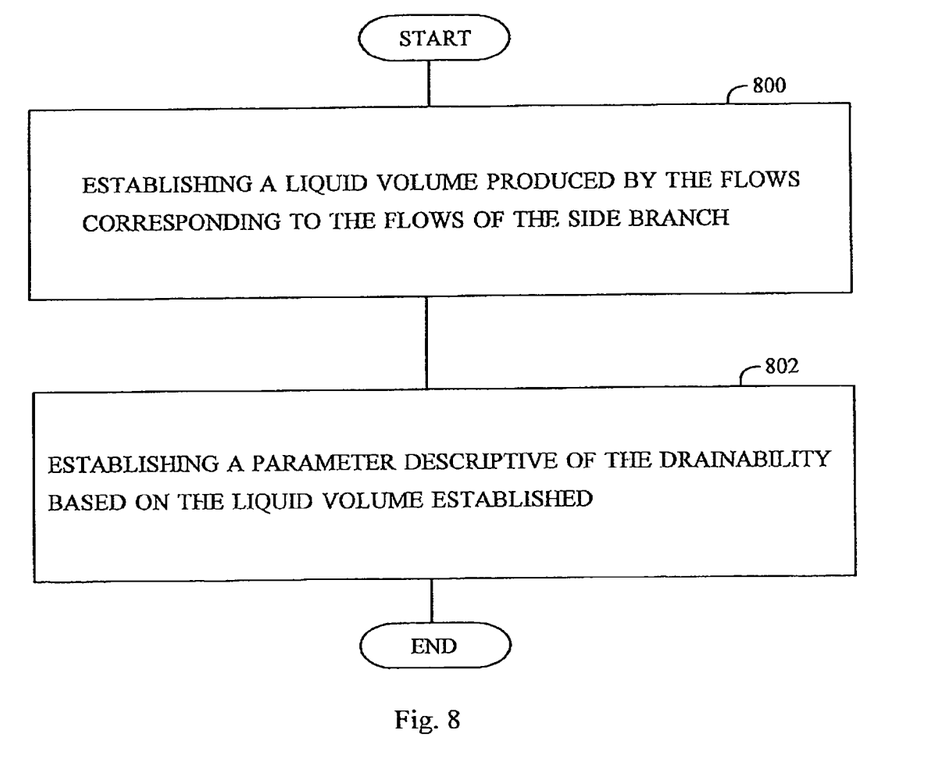
FIG. 8 shows a flow diagram of a method of establishing a liquid volume and establishing a corresponding parameter descriptive of drainability.

FIG. 8 shows a flow diagram of a method of establishing a liquid volume and establishing a corresponding parameter descriptive of drainability. In step 800, the method involves establishing a liquid volume produced by the flows corresponding to the flows of the side branch. In step 802, the method proceeds to establishing a parameter descriptive of the drainability based on the liquid volume established in step 800.

Figure 9:
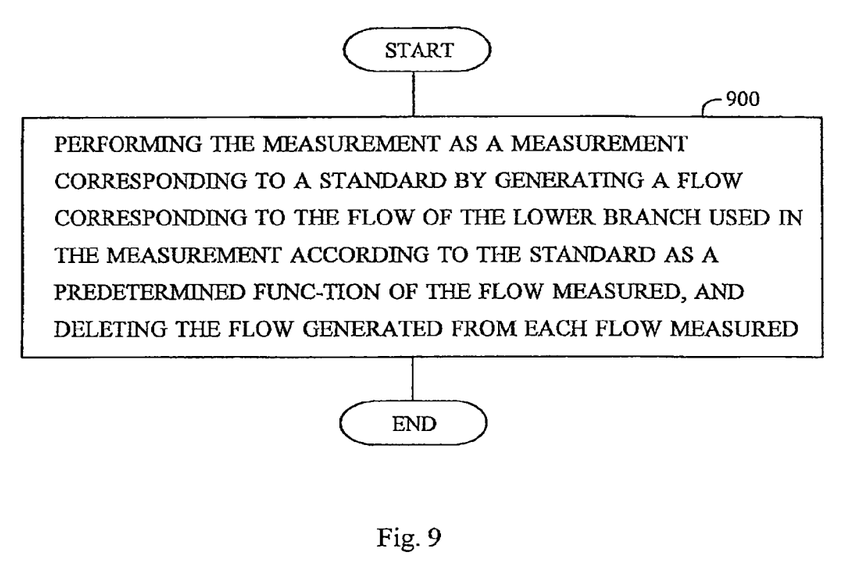
FIG. 9 shows a flow diagram of a method for performing a measurement of a suspension corresponding to a standard.

FIG. 9 shows a flow diagram of a method for performing a measurement of a suspension corresponding to a standard, In step 900, the method involves performing the measurement as a measurement corresponding to a standard by generating a flow corresponding to the flow of the lower branch used in the measurement according to the standard as a predetermined function of the flow measured, and deleting the flow generated from each flow measured.

Figure 10:
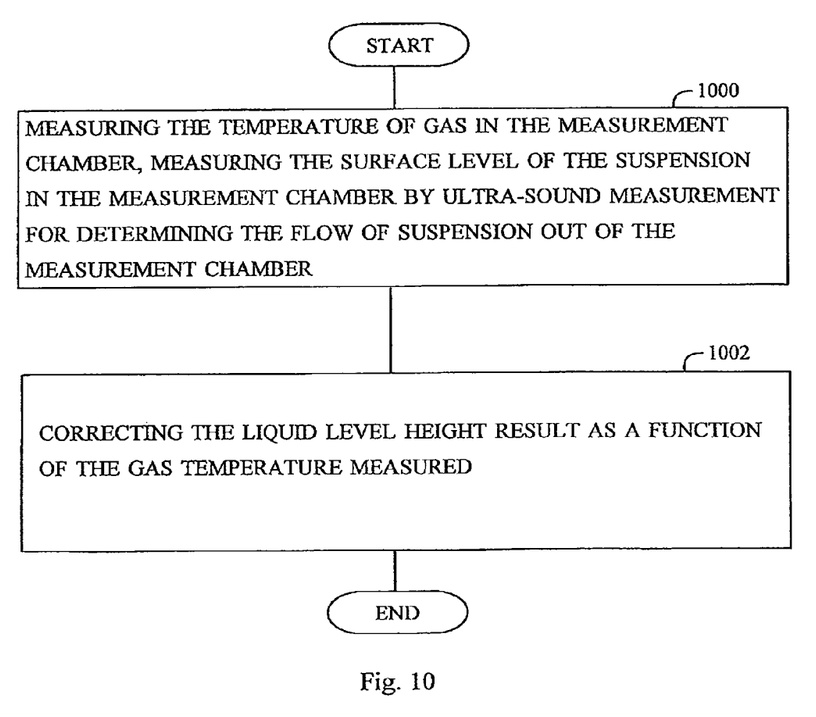
FIG. 10 shows a flow diagram of a method for measuring the temperature of gas and performing a correction based on the measured temperature.

FIG. 10 shows a flow diagram of a method for measuring the temperature of gas and performing a correction based on the measured temperature, In step 1000, the method involves measuring the temperature of gas in the measurement chamber, and measuring the surface level of the suspension in the measurement chamber by ultrasound measurement for determining the flow of suspension out of the measurement chamber. In step 1002, the method proceeds to correcting the liquid level height result as a function of the gas temperature measured in step 1000.

Figure 11:
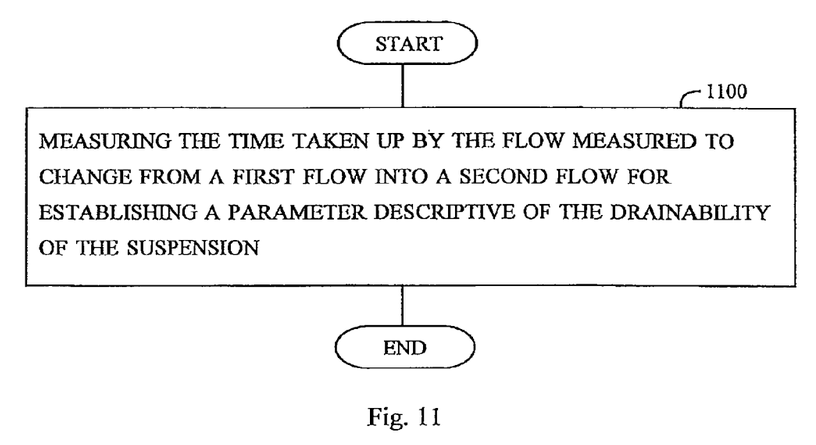
FIG. 11 shows a flow diagram of a method for measuring a time interval corresponding to a first flow changing into a second flow.

FIG. 11 shows a flow diagram of a method for measuring a time interval corresponding to a first flow changing into a second flow. In step 1100, the method involves measuring the time taken up by the flow measured to change from a first flow into a second flow for establishing a parameter descriptive of the drainability of the suspension.

Figure 12:
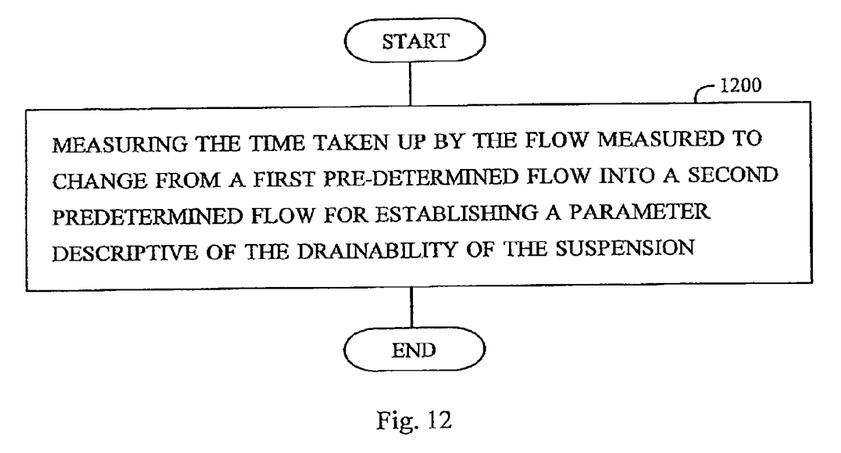
FIG. 12 shows a flow diagram of a method as in FIG. 11, where the first and second flows are predetermined.

FIG. 12 shows a flow diagram of a method as in FIG. 11, where the first and second flows are predetermined. Step 1200 involves measuring the time taken up by the flow measured to change from a first predetermined flow into a second predetermined flow for establishing a parameter descriptive of the drainability of the suspension.

The methods presented may be implemented as computer programs. Instead of a program, the solutions may be implemented as an apparatus structure by means of separate logics components or one or more application-specific integrated circuits (ASIC). A hybrid of these different implementations is also feasible.

The computer program product may be stored in a distribution medium for a computer program. The distribution medium of the computer program is readable with a computer (processor) that executes the program. The distribution medium may be any known medium with which the computer program is transferable. The distribution medium may be a medium readable with a processor, a memory, a data communication signal or a compressed program package, for example.

Although the invention is described herein with reference to the examples in accordance with the accompanying drawings, it will be appreciated that the invention is not to be so limited, but may be modified in a variety of ways within the scope of the appended claims.

What is claimed is:

1. A method of modelling the drainability measurement of a suspension, the method comprising:
   receiving known liquid flows of water or known suspension with a funnel, each of which fills the funnel in such a manner that the liquid flows from a side branch;
   measuring, for each known liquid flow received with the funnel, each flow of a lower branch and/or each flow of the side branch; and
   establishing a modelling function based on the measurements between the flows of the lower branch and/or the flows of the side branch and the known liquid flows received with the funnel.

2. A method of measuring a suspension, the method comprising
   receiving a sample of a predetermined volume in a measurement chamber;
   allowing the suspension to flow out of the measuring chamber through wire;
   measuring the flow out of the measurement chamber at least at two points in time; and
   establishing a parameter descriptive of the drainability of the suspension by a predetermined modelling function from the flows measured at the different points in time, wherein the predetermined modelling function is determined by:
   receiving known liquid flows of water or known suspension with a funnel, each of which fills the funnel in such a manner that the liquid flows from a side branch;
   measuring, for each known liquid flow received with the funnel, each flow of a lower branch and/or each flow of the side branch; and
   establishing a modelling function based on the measurements between the flows of the lower branch and/or the flows of the side branch and the known liquid flows received with the funnel.

3. A method as claimed in claim 2, the method further comprising:
   performing the measurement as a measurement corresponding to a standard by
   generating a flow corresponding to the flow of the lower branch used in the measurement according to the standard as a predetermined function of the flow measured, and deleting the flow generated from each flow measured.

4. A method as claimed in claim 2, the method further comprising:
   measuring the temperature of gas in the measurement chamber;
   measuring the surface level of the suspension in the measurement chamber by ultrasound measurement for determining the flow of suspension out of the measurement chamber; and
   correcting the liquid level height result as a function of the gas temperature measured.

5. A method as claimed in claim 2, the method further comprising:
   measuring the time taken up by the flow measured to change from a first flow into a second flow for establishing a parameter descriptive of the drainability of the suspension.

6. A method as claimed in claim 2, the method further comprising:
   measuring the time taken up by the flow measured to change from a first predetermined flow into a second predetermined flow for establishing a parameter descriptive of the drainability of the suspension.

7. A method as claimed in claim 2, the method further comprising:
   performing the measurement as a measurement corresponding to a standard by generating, from each flow measured which is larger than a predetermined flow, a flow corresponding to each flow of the side branch of the funnel used in the measurement according to the standard with a predetermined function, according to which the absolute value of the difference between the two different flows of the side branch of the funnel is less than the absolute value of the difference between the two different flows measured; and
   establishing a parameter descriptive of the drainability based on the flows corresponding to the flows of the side branch.

8. A method as claimed in claim 7, the method further comprising:
   establishing a liquid volume produced by the flows corresponding to the flows of the side branch; and
   establishing a parameter descriptive of the drainability based on the liquid volume established.

9. A measurement device for modelling the drainability measurement of a suspension, wherein the measurement device comprises:
   a funnel, a meter and a memory,
   the funnel comprising a side branch and a lower branch being configured to receive known liquid flows of water or known suspension, each of which is larger than the flow of the lower branch of the funnel;

the meter is configured to measure, for each known liquid flow received with the funnel, each liquid flow discharged from the funnel in at least one of the following: lower branch, side branch; and the memory is configured to store the modelling function, the modelling function being based on a dependency between the known liquid flows received with the funnel and the liquid flows discharged from the funnel in at least one of the following: lower branch, side branch.

10. A measurement device as claimed in claim 9, wherein the measurement device comprises a processor configured to establish a modelling function.

11. A measurement device for measuring a suspension, the measurement device comprising a measurement chamber of a predetermined volume and a wire, the measurement chamber being configured to receive a suspension sample and allow the suspension sample to flow out of the measurement chamber through the wire, wherein the measurement device comprises a sensor for measuring the flow out of the measurement chamber at least at two different points in time;

a memory, in which a predetermined modelling function is stored; and a processor configured to establish a parameter descriptive of the drainability of the suspension based on the predetermined function stored in the memory from the flows measured at the different points in time;

wherein the predetermined modelling function is determined by a measurement device for modelling the drainability measurement of a suspension, the measurement device comprising a funnel, a meter and a memory, the funnel comprising a side branch and a lower branch being configured to receive known liquid flows of water or known suspension, each of which is larger than the flow of the lower branch of the funnel;

the meter is configured to measure, for each known liquid flow received with the funnel, each liquid flow discharged from the funnel in at least one of the following: lower branch, side branch; and the memory is configured to store the modelling function, the modelling function being based on a dependency between the known liquid flows received with the funnel and the liquid flows discharged from the funnel in at least one of the following: lower branch, side branch.

12. A measurement device as claimed in claim 11, wherein the measurement device is configured to perform the measurement as a measurement corresponding to a standard in such a manner that the processor is configured to generate a flow corresponding to the flow of the lower branch from a flow measured with a modelling function and to delete the flow generated from each flow measured.

13. A measurement device as claimed in claim 11, wherein the processor is configured to measure the time taken up by the flow measured to change from a first flow into a second flow for establishing a parameter descriptive of the drainability of the suspension.

14. A measurement device as claimed in claim 11, wherein the processor is configured to measure the time taken up by the flow measured to change from a first predetermined flow into a second predetermined flow for establishing a parameter descriptive of the drainability of the suspension.

15. A measurement device as claimed in claim 11, wherein the measurement device comprises a thermometer and an ultrasound meter; the thermometer is configured to measure the temperature of gas in the measurement chamber, the ultrasound meter is configured to measure the surface height of the suspension in the measurement chamber for determining the flow out of the measurement chamber; and the processor is configured to correct the liquid level height result as a function of the gas temperature measured.

16. A measurement device as claimed in claim 11, wherein the measurement device is configured to perform the measurement as a measurement corresponding to a standard, and the processor is configured to generate a flow corresponding to each flow of the side branch of the funnel from each flow measured that is larger than a predetermined flow with a predetermined function, according to which the absolute value of the difference between two different flows of the side branch of the funnel is less than the absolute value of the difference of two different flows measured, and the processor is configured to establish a parameter descriptive of the drainability based on the flows corresponding to the flows of the side branch.

17. A measurement device as claimed in claim 16, wherein the processor is configured to establish a liquid volume produced by the flows corresponding to the flows of the side branch; and the processor is configured to establish a parameter descriptive of the drainability based on the liquid volume established.

* * * * *